United States Patent [19]

Pierson

[11] Patent Number: 4,982,743
[45] Date of Patent: Jan. 8, 1991

[54] ITCH REDUCER

[76] Inventor: Marlin R. Pierson, 7010 Chicago Ave., Richfield, Minn. 55423

[21] Appl. No.: 497,702

[22] Filed: Mar. 23, 1990

[51] Int. Cl.$^5$ .............................................. A61N 1/00
[52] U.S. Cl. .................................. 128/800; 128/419 R
[58] Field of Search ............... 128/800, 801, 802, 783, 128/419 R

[56] References Cited

U.S. PATENT DOCUMENTS

| | | |
|---|---|---|
| 870,927 | 11/1907 | Boyd . |
| 2,447,127 | 8/1948 | Landauer . |
| 2,659,372 | 11/1953 | Andresen . |
| 3,424,165 | 1/1969 | Moss . |
| 3,900,018 | 8/1975 | Piunno . |
| 4,033,356 | 4/1977 | Hara ...................... 128/405 |
| 4,083,965 | 4/1978 | Bluhm ...................... 428/128 |
| 4,180,079 | 12/1979 | Wing ...................... 128/422 |
| 4,688,140 | 8/1987 | Hammes ...................... 361/232 |
| 4,691,264 | 9/1987 | Schaffhauser et al. ............. 361/232 |
| 4,741,347 | 5/1988 | Robert et al. ...................... 128/800 |
| 4,797,402 | 1/1989 | Dorsey ...................... 514/171 |
| 4,823,810 | 4/1989 | Dervieux ...................... 128/783 |

Primary Examiner—Lee S. Cohen
Assistant Examiner—Scott M. Getzow
Attorney, Agent, or Firm—Robert C. Baker

[57] ABSTRACT

The new low voltage itch reducer is characterized by having a treatment head comprising a body of electrically insulating material having a substantially flat face surface. A pattern of spaced electrode tips project outwardly from the face surface. The pattern includes electrode tips of opposite polarity in sufficiently spaced relationship so that discharge of electrical current through the air between tips of opposite polarity does not occur under the low voltage employed. The electrode tips at the edges of the pattern define the perimeter of it. The pattern has no face dimension greater than about 20 millimeters. The outward projection of the electrode tips is substantially equal for all tips of the pattern. Pressing the treatment head against a person's skin over an itching insect bits effectively permits the flat surface of the body of the head to contact the skin of the individual with the electrodes pressing into the skin, without penetrating the skin, over the insect bite.

12 Claims, 1 Drawing Sheet

ITCH REDUCER

BACKGROUND OF THE INVENTION

This invention relates to a low voltage itch reducer for insect bites, and more particularly to an extraordinarily compact battery powered low voltage itch reducer especially useful for reducing the itch of mosquito bites.

Fishermen and hunters and other outdoor-loving persons are all too familiar with the itch problems caused by mosquito bites. Lotions and sprays to ward off mosquitoes have their place but are not completely effective. Just one bite of a mosquito can command dominant attention and scratching; and several bites can cause even the most avid outdoor-lover to give thought to returning indoors before originally planned. It is not the extraordinary pain of the mosquito bite; it is the annoyance and distraction that it causes. But relieving the modest pain, that is, relieving the itch sensation, is critical to obviating the annoyance and distraction.

Insofar as is known, no one has heretofore provided a simple compact and effective insect bite itch reducer operable on continuous direct current from a low voltage battery.

Heretofore it has been known to employ jolts of electricity, particularly of relatively high voltage even in excess of 20,000 volts, for the purpose of neutralizing snake bites. The phenomenon of snake bite neutralization by high voltage jolts is not fully understood. Some believe that the high voltage and low amperage ionizes the venom or components of the venom. Advocates for this treatment for snake bites however stress that only exceedingly high voltage jolts are useful.

Electrical appliances for therapeutic treatments, insofar as is known, use relatively high voltage jolts of electricity; and none is known to have projecting electrodes of opposing polarity in a confined pattern on a treatment head, as taught herein.

SUMMARY OF THE INVENTION

The new low voltage itch reducer is characterized by having a treatment head comprising a body of electrically insulating material having a substantially flat face surface. A pattern of spaced stiff electrode tips project outwardly from the face surface. The pattern includes electrode tips of opposite polarity in sufficiently spaced relationship so that discharge of electrical current through the air between tips of opposite polarity does not occur under the low voltage and low amperage employed. The electrode tips at the edges of the pattern define the perimeter of it. The pattern has no face dimension greater than about 20 millimeters. The outward projection of the electrode tips is substantially equal for all tips of the pattern. Pressing the treatment head against a person's skin over an itching insect bite effectively permits the flat surface of the body of the head to contact the skin of the individual with the electrodes pressing into the skin, without penetrating the skin, over the insect bite. Held in this position for about one minute, sometimes as short as 30 seconds or less, the continuous electrical direct current of low voltage flows between the electrode tips of opposing polarity through insect bite infected tissue of the person and reduces or totally neutralizes the itching of the bite despite the low voltage electrical energy employed. The fact of active electrical direct and continuous current flow is not readily apparent to or felt by a user; but the relief of itching is apparent and welcome.

The utility of the new itch reducer is most apparent in reducing and even completely neutralizing the itch of mosquito bites. No apparent reason exists for it not to be useful for reducing the itch of other small insect bites. The new itch reducer is not recommended for use on extremely venomous bites such as those of the snake or scorpion variety.

DESCRIPTION OF THE PREFERRED EMBODIMENT

Figure 1:
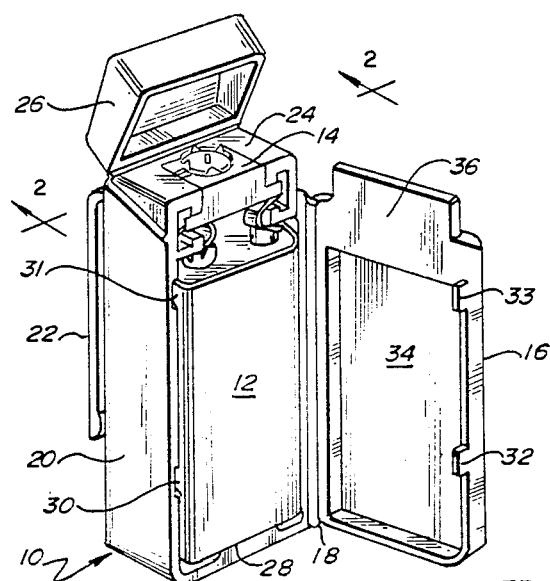
FIG. 1 is a schematic perspective view of the new itch reducer, illustrated with its battery door ajar and its head-protecting cover in partially opened condition.

Referring particularly to FIG. 1, the new itch reducer comprises a relatively or substantially thin-walled housing 10 having an internal recess for accommodating a low voltage battery 12 such as one of 9 volts. The housing is preferably of just sufficient size to accommodate a 9 volt battery and the treatment head structure 14. The front wall of the housing is integral with the door 16 for covering the access opening of the battery chamber. The housing is preferably molded out of organic plastic material of electrically insulative character; and the hinge 18 for the battery door 16 is suitably formed by a thin connection of plastic between the largest or main portion of the housing 10 and the battery door 16. Such thin plastic hinges are sometimes referred to as living hinges.

A left side wall 20 of the housing has its counterpart, a right side wall, in opposing relationship. Fixed in the back wall of the housing is a clip member 22 suitably formed of molded plastic. Clip 22 is adapted to be slipped over an edge of a structure such as a pocket or belt to hold the itch reducer product in handy readiness for use. The upper wall 24 of the housing incorporates the treatment head structure 14.

A cover 26 is suitably hinged by a thin connection of plastic, as a living hinge, at one edge of the upper wall 24 or at a location near an edge of the upper wall. A cover is especially desirable to protect against accidental conductive contact caused by foreign objects between the electrode tips of opposite polarity on the treatment head structure and resulting needless loss of battery power. No switch for turning off electrical supply to the electrodes of the treatment head is needed, but since the electrodes are conveniently always charged, it is important to protect them from accidental contact with conductive material and resulting waste of battery power. Of course a switch addition is optional, but not needed. The cover also serves as a protector against accidental scratching of human tissue when the itch reducer is stored in one's pocket.

The bottom wall of the housing 10 is suitably provided with a small elevated plateau or ridge 28 of plastic for strength; and this ridge also functions to maintain the battery terminals in pressurized contact against spring-like electrode connectors to be discussed.

A special feature of the housing is that the left side wall 20 or side wall opposite the side wall carrying the living hinge for the battery door is suitably provided with grooved recesses 30 and 31 adapted to receive, in a friction-like manner, knob-like locking projections 32 and 33 of the battery door. Also to be noted is that the battery door 16 extends above the modest recess 34 in it for accommodating a fraction of the battery when the door is closed. The upper part 36 of the battery door is formed with a flat or planar interior surface which mates in flush manner against the elements forming the upper end (above the battery) of the main housing body. The design of the housing, as illustrated, makes for ease of molding of the cover 26 and its living hinge, as well as the battery door 16 and its living hinge, at the same time and integrally with the main housing portion. Further, the design is such that when the cover 26 is closed over the upper end of the product after the battery door 16 has been closed, the battery door is locked against being opened because the front edge of the cover extends over the upward projection 36 of the battery door.

Figure 2:
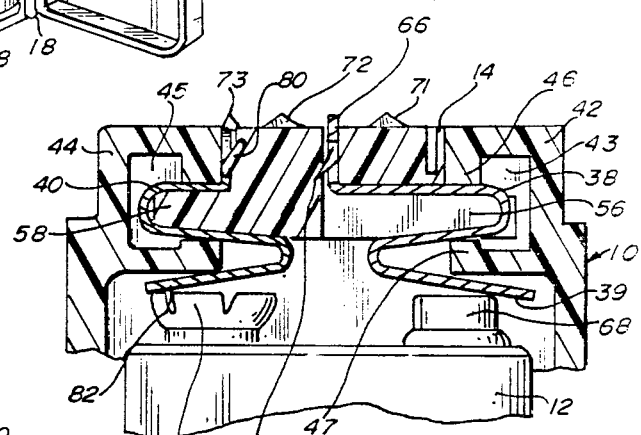
FIG. 2 is a schematic cross sectional view through the vertical plane of 2—2 of FIG. 1, illustrating the treatment head structure, with other parts broken away.
Figure 3:
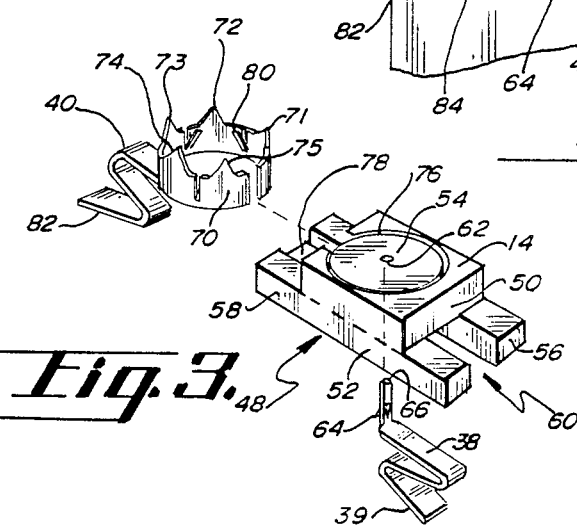
FIG. 3 is a schematic exploded perspective view of three basic elements making up the treatment head structure of FIGS. 1 and 2.

FIGS. 2 and 3 deal with details of structure for the treatment head and upper housing part and will be discussed together.

The treatment head 14, including the electrode structures 38 and 40 associated with it (see FIG. 3), is designed to be slidably inserted in the upper part of the housing 10. The upper part of the housing 10 has opposing inwardly-directed C-shaped structures 42 and 43 integral with the plastic of the main part of the housing. The C-shaped structures provide lateral cavities at each side of the upper portion of the housing. In this sense, the C-shaped structures could be in essence U-shaped; but suffice it to say that lateral cavities extend from the vertical front face of the main portion of the housing to the wall forming the back of the housing. These cavities are parallel to each other and perpendicular to the back and front of the housing. The C-shape structures 42 and 44 provide spaced upper and lower leg portions (marked 46 and 47 for the C-structure 42) which function more or less as a clamp, as will be evident.

The treatment head structure comprises a body portion 48 and two electrode structures, a first electrode structure 38 and a second electrode structure 40. (More electrode structures are optional.) The first and second electrode structures are assembled with the block body 48 of the treatment head and the complete assembly is slidably mounted in the upper part of the housing in a manner such that the upper and lower legs of the C-shape structures 42 and 44 at the sides of the interior of the housing function more or less to clamp the assembly of the two electrodes and treatment head body into position and complete the assembly details for making the most preferred embodiment of the invention.

The body 48 of the treatment head is suitably molded out of or cut from electrically insulating organic plastic. Polyvinyl chloride organic plastics are generally suitable, but even polyethylene can be suitable—not only for the body of the treatment head but for the entire housing and its cover and door. Any of a variety of plastics may be employed as satisfactorily electrically insulative at the low voltages and amperages employed. While body 48 is block-like in character, it has certain special features for the most preferred embodiment. It has a super structure 50 and a base part 52. A horizontal dash line in FIG. 3 shows the location of a hypothetical plane between the super structure 50 from the base part 52. The super structure and base part each has parallel lateral sides and parallel front and back sides. The upper surface 54 of the super structure is substantially flat and forms the substantially flat face 54 of the treatment head. The super structure 50 is integral with a base part 52. The base part 52 extends outwardly at its lateral sides or lateral edges more than the super structure. The opposite side outward lateral extensions 56 and 58 function more or less as locking ears which pass between and are lodged between the upper and lower legs of the C-structures 42 and 44 when the elements of FIG. 3 are assembled and put in the upper end of the housing.

An open channel 60 extends entirely through (from top to bottom) the right lateral base extension 56 (thus dividing that extension into front and back parts). Channel 60 extends in the base part 52 to approximately the center portion of, or half way across, the base part of the block body 14. This in effect causes the super structure 50 to bridge across a portion of the open channel 60. Further, a central hole 62, or very thin opening, extends vertically through the super structure from face 54 to the lateral channel 60 of the base 52. The first electrode structure 38, is accommodated in channel 60 and the hole 62.

The first electrode structure 38 is illustratively formed as a single strip or band from electrically conductive metal. Metal alloy electrodes of suitable electrical conductivity are preferred. They should be non-corrosive. The most preferred alloys are those having at least some ability to behave as a leaf spring in thin sections. The electrode may be formed by stamp cutting from a flat sheet of the conductive metal, following which the stamped band or strip is bent in a serpentine manner, as illustrated, except for an upstanding electrode portion having a barb 64 pressed out from it. The upstanding portion terminates at an electrode tip 66. The tip is pressed through the central hole 62 of the super structure 50 until the wide section of the strip of metal (at a right angle to the bottom of the upstanding portion, as shown) abuts the bottom of the super structure. Simultaneously, the barb 64 of the upstanding electrode portion is forced to dig itself into the wall of plastic at the hole of the super structure. This locks the electrode in position and the serpentine remaining connecting portion of the electrode band extends into the battery recess of the housing for pressing contact at its remote end 39 against the positive terminal 68 of the battery 12.

The second electrode structure 40 likewise is suitably formed from a flat sheet of electrically conductive metal by stamp cutting. The stamping of it in flat form is such that it is in the shape of a T, with the cross-bar 70 of the T having spaced electrode tips 71, 72, 73, 74, and 75 projecting upwardly from the upper edge of the cross-bar. Barbs 80 are simultaneously stamped in the cross-bar so that the upper end of the barbs extends outwardly or is pressed outwardly from the strip or band of the cross-bar. The stamped piece is then bent and shaped into the form illustrated in FIG. 3, with the cross-bar portion 70 of the T arranged in a circular manner and with the stem or leg of the T put in serpentine form. The super structure 50 of the block body has a generally circular or substantially circular very thin slot 76 cut or molded into it from the top flat surface 54 of it. A lateral groove 78 is suitably cut or molded into the top surface only of the left lateral extension 58 of the base portion 52 of the block body 48. Groove 78 extends inward only to the generally circular slot 76 into the face 54 of the super structure. The circular cross-bar portion 70 of the second electrode 40 is then pressed into the slot 76 of the super structure and the barbs 80 of the circular band or cross-bar lock themselves into the walls of the slot 76 so as to fix the electrode in the super structure, and thereby fix the projecting electrode tips 71–75 above the flat face surface 54 of the super structure. The connecting band of the electrode lies in the groove 78 of the base of the block and the serpentine contour of the band extends into the battery recess, as illustrated in FIG. 2, for spring like pressure contact at its end 82 against the negative terminal 84 of the battery.

The electrode tips are relatively dull in the sense that they do not present a sharp or pin-like cutting edge. They are not truly flexible or easily bent. They are relatively rigid or stiff, and depress the skin of a person but do not penetrate or puncture the skin in use. They are most preferably relatively small in cross-section, not over about a square millimeter or so in cross-section at their projecting end part.

Also to be noted is that each electrode structure incorporates a connector which is in electrically conductive relationship with a terminal of the battery in the battery recess.

Further, each electrode structure is mounted or carried by body 48 in insulatively spaced relationship from the other. Each electrode tip of one polarity is spaced sufficiently from the electrode tip or tips of the other polarity so as to avoid electrical discharge through the air between the tips of opposite polarity. This spacing however is not very great and will vary depending on variation of battery voltage which may be as low as a couple volts up to about 20 volts, with 9 volt batteries preferred. The spacing between electrode tips of opposite polarity is at least about 0.5 millimeters, even more preferably at least about 1 millimeter, but is not in excess of about 10 millimeters and preferably not in excess of about 5 millimeters. Ideally the spacing should not exceed about 3 or 4 millimeters. The reason for this very limited but effective spacing is so that electrical current of low voltage will flow through human tissue between the electrode tips of opposite polarity when the dull tips are pressed into the skin of a person without puncturing the skin.

It is essential that the electrode tips be able to project outwardly from the face surface of the treatment head. However, the distance of projection, while necessarily sufficient to cause a depression into the skin of an individual when the plastic of the treatment head is pressed against a persons skin, should not be so great as to create a hazard from careless use of the device. The degree of outward projection must be at least about 0.2 millimeters, but need not and should not exceed about 1 millimeter. The distance of outward projection should be substantially the same for all electrode tips of the pattern. If necessary a finish step of grinding the tips to equalize the outward projection can be done. Suitably the electrodes at portions beneath the tips are fixedly mounted in the body mass 48.

Importantly, the electrode tips of the treatment head should be grouped together or concentrated in what might be called a pattern. The reason for this is because of the low voltages employed, plus the convenient fact that the swelling of mosquito bites is generally of limited area. Excessive spacing distribution of the electrode tips would tend to nullify effectiveness at the low voltages and amperages employed. The outside perimeter of the pattern is defined by the outermost tips at the edges of the pattern on the treatment head. The perimeter of the pattern should not have any dimension (measured parallel with the face surface of the head) less than about 5 millimeters and should not have any dimension greater than 20 millimeters, preferably not greater than about 10 or 12 millimeters.

Relief from itching arises when the device of the invention is used as described. A dead battery in the device must be replaced with a live active one. Relief does not come from merely dispersing the fluid of a mosquito bite. It comes from electrical modification of the fluid of the insect bite as electrical current flows through it.

Figure 4:
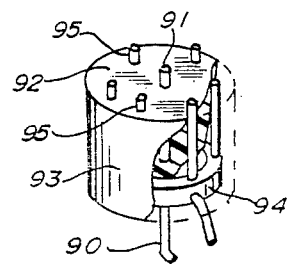
FIG. 4 is a schematic perspective view of an alternative treatment head structure, with parts broken away.

Within the ambit of this invention are treatment heads formed by molding the plastic of insulative character about the electrode structures. This feature of the invention is illustrated in FIG. 4 where a first electrode structure 90 such as one of positive polarity presents an exposed electrode tip 91 above the flat face surface 92 of the head body 93 and a second electrode structure 94 such as one of negative polarity has a plurality of electrode extensions presenting plural exposed electrode tips 95 in a circumferential arrangement about and spaced from the electrode tip 91 of positive polarity. Molding the insulative plastic forming head 93 can be accomplished after jigging the electrode structures in spaced relationship. Molding provides a secure fixing of the electrode structures in the plastic with a pre-determined outward projection of the electrode tips above the flat surface 92 of the body.

Similarly, the first and second electrode structures illustrated in FIG. 3 maybe formed and placed in a mold subsequently filled with the plastic insulative material forming the block body 48 of FIG. 3, either in the identical form illustrated in FIG. 3 or in a modified form such that the plastic fills or covers a portion of the band connectors of the electrode structures.

While simplicity of manufacture has been a consideration in describing this invention, and the preferred approach is that of forming unitary electrode structures wherein the connecting link for battery terminals is part of the same, it will be appreciated that composite electrode structures of the type illustrated or effective functional equivalents may be formed by soldering parts together. The term electrode structure as used herein therefore is intended to embrace not only unitary stamped structures incorporating connector elements for battery terminals but also those where the connector for battery terminals may be by way of wires suitably insulated as needed and by way of special and more or less conventional male and female snap on elements for mating relationship with terminals of conventional 9 volt batteries as available on the market.

Thus the invention may be embodied in other specific forms than illustrated without departing from the spirit or essential characteristics of it. The illustrated embodiment is preferred; the scope of the invention is indicated by the appended claims rather than by the foregoing description. All changes which come within the meaning and range of equivalency of the claims are intended to be embraced thereby.

That which is claimed:

1. A low voltage itch reducer characterized by a treatment head comprising a body of electrically insulating material having a substantially flat face surface and spaced electrode structures of opposite polarity carried by said body, said electrode structures providing a pattern of a plurality of spaced electrode tips projecting outwardly from the face surface of said body, said electrode tips at the edges of said pattern defining the perimeter of said pattern, said pattern perimeter having no face dimension greater than about 20 mm, the outward projection of said electrode tips being substantially equal for all electrode tips of said pattern, the spacing distance between electrode tips of opposite polarity being sufficient to prevent electrical discharge through the air between opposite polarity tips at low voltages up to about 20 volts and being at least about 0.5 mm, and the projection of said electrode tips being such that pressing said head on the skin of a person over an insect bite effectively permits the flat surface of the body of the head to contact the skin with the electrode tips pressing into the skin over the insect bite without puncturing the skin, thereby to cause electrical current flow through the insect bite for reducing the itching of the bite.

2. The itch reducer of claim 1 wherein the outward distance of projection of said electrode tips from the flat face surface of said body is at least about 0.2 mm and not greater than 1 mm.

3. The itch reducer of claim 1 wherein the spacing distance between electrode tips of opposite polarity is no greater than about 10 mm.

4. The itch reducer of claim 1 wherein said body comprises molded plastic material.

5. A low voltage itch reducer comprising an electrically insulative housing having a battery recess, a battery of no more than 20 volts having spaced first and second terminals of opposite polarity in said recess, and a treatment head mounted in a wall of said housing, said treatment head comprising
 a body of electrically insulative material having a substantially flat face surface at the exterior of said housing,
 a first electrode structure carried by said body and having at least one relatively dull electrode tip projecting outwardly from the face surface of said body, said first electrode structure including a connector in electrically conductive relationship with the first terminal of said battery,
 a second electrode structure including a connector in electrically conductive relationship with the second terminal of said battery, said second electrode structure being carried by said body in insulatively spaced relationship from said first electrode structure, said second electrode structure having a plurality of relatively dull electrode tips projecting outwardly from the face surface of said body in sufficiently spaced relationship from any and all electrode tips of said first electrode structure to avoid electrical discharge through the air between said tips of opposite polarity, said spacing between tips of opposite polarity being such that electrical current of low voltage flows between said tips of opposite polarity through a mosquito bite when said tips are pressed on the bite area of the skin of a person,
 said outward projection of said electrode tips being in a pattern within an area on said face surface having a minimum dimension of 5 mm and a maximum dimension of 20 mm, the outward projection of said electrode tips being substantially equal and sufficient to cause a depression into the skin of a person without puncture of the skin when said treatment head is pressed on the skin over an itch caused by a mosquito bite.

6. The itch reducer of claim 5 wherein said first electrode structure in its entirety consists of a unitary continuous strip of electrically conductive material.

7. The itch reducer of claim 5 wherein said second electrode structure in its entirety consists of a continuous strip of electrically conductive material, said continuous strip having a substantially T-shape in flat form and having the cross-bar portion of the T-shape curved and pressed into a generally circular slot in the face of said body of electrically insulative material.

8. The itch reducer of claim 5 wherein said body of electrically insulative material has a relatively centered opening extending therethrough perpendicular to the face surface thereof and a generally circular slot about said centered opening and extending into said body from the face surface thereof, said first electrode structure in its entirety consisting of a unitary continuous strip of electrically conductive material having one end terminating as said electrode tip thereof, said one end being pressed through said centered opening of said body to expose the electrode tip thereof on the face surface of said body, and wherein said second electrode structure in its entirety consists of a unitary continuous strip of electrically conductive material having a substantially T-shape in flat form with said electrode tips extending from the upper edge of the cross-bar of the T-shape, and having the cross-bar portion of the T-shape curved and pressed into the generally circular slot in the face of said block to such a degree that only the electrode tips at the upper edge of the cross-bar of the T-shape project above the face surface of said body.

9. The itch reducer of claim 5 wherein said housing is equipped with a hinged battery door for said battery recess and said housing is equipped with a cover member for placement over said treatment head.

10. The itch reducer of claim 9 wherein said cover member when placed over said treatment head locks said battery door in closed condition.

11. The itch reducer of claim 5 wherein the outward distance of projection of said electrode tips from the flat face surface of said body is at least about 0.2 mm and not greater than 1 mm.

12. The itch reducer of claim 5 wherein the spacing distance between electrode tips of opposite polarity is no greater than about 10 mm.

* * * * *